(12) United States Patent
Sugiyama

(10) Patent No.: US 8,873,708 B2
(45) Date of Patent: Oct. 28, 2014

(54) RADIOGRAPHIC IMAGE CAPTURING DEVICE AND METHOD

(75) Inventor: Shinko Sugiyama, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 915 days.

(21) Appl. No.: 12/999,299

(22) PCT Filed: Jun. 11, 2009

(86) PCT No.: PCT/JP2009/002658
§ 371 (c)(1),
(2), (4) Date: Dec. 15, 2010

(87) PCT Pub. No.: WO2009/153947
PCT Pub. Date: Dec. 23, 2009

(65) Prior Publication Data
US 2011/0085642 A1 Apr. 14, 2011

(30) Foreign Application Priority Data
Jun. 17, 2008 (JP) ................................ 2008-158457

(51) Int. Cl.
*A61B 6/00* (2006.01)
*H05G 1/64* (2006.01)
*A61B 6/06* (2006.01)

(52) U.S. Cl.
CPC ............... *A61B 6/504* (2013.01); *A61B 6/4225* (2013.01); *A61B 6/542* (2013.01); *A61B 6/06* (2013.01); *A61B 6/4441* (2013.01); *A61B 6/481* (2013.01)
USPC ............................... 378/62; 378/151; 382/130

(58) Field of Classification Search
CPC ........ A61B 6/06; A61B 6/4441; A61B 6/504; A61B 6/542; G21K 1/04; G21K 1/046
USPC ...................... 378/8, 41, 42, 62, 91, 95, 98.7, 378/150–153, 205; 382/130
See application file for complete search history.

(56) References Cited

U.S. PATENT DOCUMENTS

| | | | | |
|---|---|---|---|---|
| 5,260,984 A | * | 11/1993 | Horbaschek | 378/150 |
| 5,412,704 A | * | 5/1995 | Horbaschek | 378/98.2 |
| 5,493,597 A | * | 2/1996 | Gotoh et al. | 378/98.2 |
| 5,539,798 A | * | 7/1996 | Asahina et al. | 378/98.5 |
| 5,768,405 A | | 6/1998 | Makram-Ebeid | |

(Continued)

FOREIGN PATENT DOCUMENTS

| | | |
|---|---|---|
| JP | 5-260381 A | 10/1993 |
| JP | 7-143977 A | 6/1995 |
| JP | 10-234714 A | 9/1998 |

*Primary Examiner* — Allen C. Ho
(74) *Attorney, Agent, or Firm* — Canon USA, Inc. IP Division

(57) ABSTRACT

A radiographic image capturing device includes a capturing unit that captures a radiographic image based on radiation (for example, X-rays) which penetrates through an object. A system control section extracts one still image from the radiographic image that is captured by the capturing unit, and displays the extracted still image on a second display section of a graphical user interface. The system control section displays a mark on a predetermined portion, which corresponds to a portion to be subjected to surgery, of the still image that is displayed on the second display section. When the mark that is displayed on the still image is selected, the system control section performs control of capturing an image of a corresponding portion of the object that corresponds to the predetermined portion using the capturing unit.

17 Claims, 13 Drawing Sheets

(56) References Cited

U.S. PATENT DOCUMENTS

| | | | |
|---|---|---|---|
| 5,872,861 A | 2/1999 | Makram-Ebeid | |
| 6,175,614 B1 * | 1/2001 | Jensen et al. | 378/98.7 |
| 6,318,892 B1 * | 11/2001 | Suzuki et al. | 378/197 |
| 6,463,121 B1 * | 10/2002 | Milnes | 378/62 |
| 6,501,826 B1 * | 12/2002 | Kropfeld | 378/98.12 |
| 6,512,808 B2 * | 1/2003 | Klingenbeck-Regn | 378/18 |
| 6,720,966 B2 * | 4/2004 | Barth et al. | 345/424 |
| 6,823,204 B2 * | 11/2004 | Grass et al. | 600/407 |
| 6,922,457 B2 * | 7/2005 | Nagata et al. | 378/19 |
| 6,947,784 B2 * | 9/2005 | Zalis | 600/425 |
| 6,959,067 B2 * | 10/2005 | Rasche et al. | 378/8 |
| 7,054,406 B2 * | 5/2006 | Ikeda et al. | 378/8 |
| 7,076,027 B2 * | 7/2006 | Matsumoto | 378/98.8 |
| 7,145,982 B2 * | 12/2006 | Ikeda et al. | 378/16 |
| 7,162,064 B2 * | 1/2007 | Klingenbeck-Regn | 382/131 |
| 7,502,445 B2 * | 3/2009 | Shi et al. | 378/115 |
| 7,522,701 B2 * | 4/2009 | Jensen et al. | 378/62 |
| 7,583,782 B2 * | 9/2009 | Yamazaki | 378/4 |
| 7,634,308 B2 * | 12/2009 | Ogawa | 600/431 |
| 7,725,163 B2 * | 5/2010 | Schmitz et al. | 600/425 |
| 7,778,688 B2 * | 8/2010 | Strommer | 600/424 |
| 7,929,743 B2 * | 4/2011 | Khorasani | 382/128 |
| 8,005,284 B2 * | 8/2011 | Sakaguchi et al. | 382/131 |
| 8,467,498 B2 * | 6/2013 | Ohishi | 378/98.12 |

* cited by examiner

601

701
702

| MARK \ ATTRIBUTE | SHAPE | COLOR (INITIAL COLOR) | POSITION INFORMATION AND SIZE INFORMATION |
|---|---|---|---|
| MARK 1 | CIRCLE | RED | (X1, Y1) L1 |
| MARK 2 | CIRCLE | RED | (X2, Y2) L2 |
| MARK 3 | CIRCLE | RED | (X3, Y3) L3 |

| MARK ID | ATTRIBUTE / POSITION INFORMATION AND SIZE INFORMATION | CAPTURE STATE | CAPTURE TIME | X-RAY DOSE | FINAL FRAME |
|---|---|---|---|---|---|
| MK001 | M1P1(X1, Y1), M1P2(X2, Y2), M1P3(X3, Y3), M1P4(X4, Y4), M1P0(X0, Y0), M1L | CAPTURED | 20 min | 0.14 mSv | |
| MK002 | M2P1(X1, Y1), M2P2(X2, Y2), M2P3(X3, Y3), M2P4(X4, Y4), M2P0(X0, Y0), M2L | BEING CAPTURED | | | |
| MK003 | M3P1(X1, Y1), M3P2(X2, Y2), M3P3(X3, Y3), M3P4(X4, Y4), M3P0(X0, Y0), M3L | HAS NOT BEEN CAPTURED | | | |

RADIOGRAPHIC IMAGE CAPTURING DEVICE AND METHOD

TECHNICAL FIELD

The present invention relates to a radiographic image capturing device including a capturing unit that captures a radiographic image based on radiation which penetrates through an object, and a radiographic image capturing method.

BACKGROUND ART

Hitherto, X-ray image capturing devices that capture images capturing of objects using X-rays, which are a type of radiation, thereby obtaining X-ray images, have become widespread mainly in medical fields. More particularly, interventional radiology (IVR) has become widespread in sites of medical treatment. In the IVR, a person (a doctor) that performs surgery finds a vascular occlusion portion or cancer cells of an object using angiography, and the person treats the vascular occlusion portion or the cancer cells using a balloon or a stent that is inserted into a blood vessel of the object under fluoroscopy. In the IVR, because insertion of a balloon or a stent into an object (a subject person) or control of the balloon or the stent needs to be performed under fluoroscopy, an X-ray image capturing device including a television (TV) system is used. In the above-mentioned IVR, a contrast medium is injected into a blood vessel (for example, a coronary artery) of a portion, which is to be subjected to surgery, of an object, and capturing of a fluoroscopic image (a radiographic image) of the portion to be subjected to surgery is performed. A person (a doctor) that performs surgery treats a vascular occlusion portion, cancer cells, or the like using a balloon or a stent while the person is looking at the captured fluoroscopic image (radiographic image). In this case, in order to carefully look at the portion to be subjected to surgery, a system in which a portion of a fluoroscopic image is specified and in which the specified portion is displayed in an enlarged manner has been proposed, for example, as disclosed in Patent Citation 1 given below.

However, in a case in which a treatment act using the IVR is performed, when only a portion, which is to be subjected to surgery, of an object is displayed in an enlarged manner, it is difficult to grasp a position at which the portion to be subjected to surgery is located on a portion (for example, the heart), whose image should be captured, of the object. Accordingly, there is a probability that efficiency of the treatment act is reduced. For this reason, typically, it is necessary to capture an image of the entirety of the portion whose image should be captured. As a result, there is a problem that the dose of X-rays (radiation) with which the object (a subject person) is irradiated is increased.

Patent Citation 1: Japanese Patent Laid-Open No. 5-260381

DISCLOSURE OF INVENTION

The present invention has been made in consideration of the above situation, and has as its object to make it possible to grasp the positional relationships between a portion, whose image should be captured, of an object and a portion, which is to be subjected to surgery, of the object, and to realize reduction in dose of radiation with which the object is irradiated.

According to the present invention, the foregoing object is attained by providing a radiographic image capturing device including the following elements: a capturing unit configured to capture a radiographic image based on radiation that penetrates through an object; an extraction unit configured to extract one still image from the radiographic image that is captured by the capturing unit; a still-image display control unit configured to perform control of displaying the still image that is extracted by the extraction unit on a user interface;
a mark display control unit configured to perform control of displaying a mark on a predetermined portion of the still image that is displayed on the user interface; and a capture control unit configured to perform, when the mark displayed on the still image is selected, control of capturing an image of a corresponding portion of the object that corresponds to the predetermined portion using the capturing unit.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF EMBODIMENT

Preferred embodiments of the present invention will be described in detail in accordance with the accompanying drawings.

In each of the embodiments of the present invention that are described below, an example of an X-ray image capturing device in which X rays are applied as radiation is shown. However, the present invention is not limited to the X-ray image capturing device. For example, a radiographic image capturing device that captures a radiographic image based on another type of radiation such as alpha rays, beta rays, or gamma rays can also be applied.

First Embodiment

First, a first embodiment of the present invention will be described.

Figure 1:
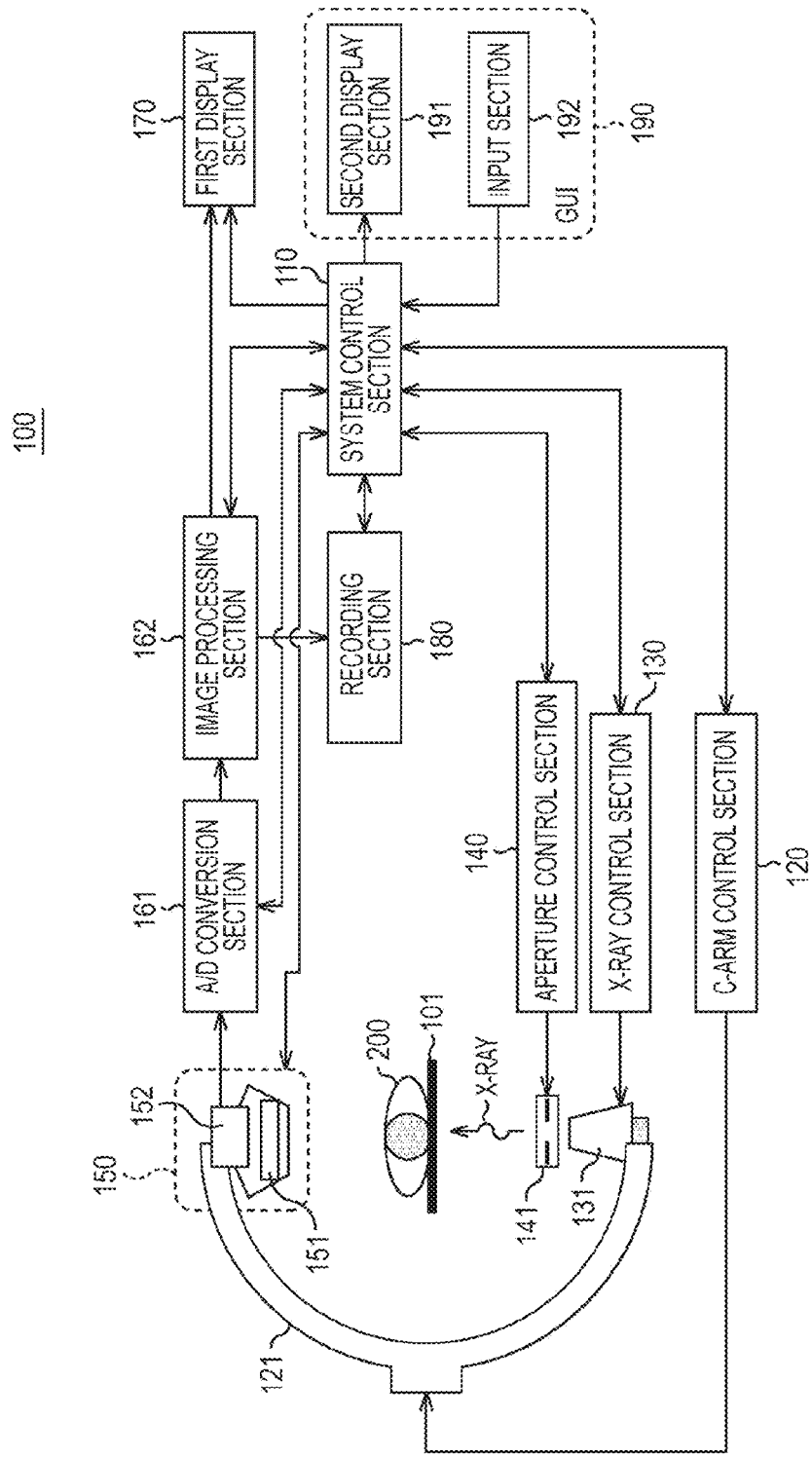
FIG. 1 is a diagram showing an example of a schematic configuration of an X-ray image capturing device (a radiographic image capturing device) according to a first embodiment of the present invention.

FIG. 1 is a schematic diagram showing an example of a schematic configuration of an X-ray image capturing device (a radiographic image capturing device) according to the first embodiment of the present invention. In this case, because an X-ray image capturing device 100 shown in FIG. 1 captures an X-ray image that is used for a diagnosis of an object 200, the X-ray image capturing device 100 can also be referred to as an "X-ray image diagnostic device".

As shown in FIG. 1, a top board 101 and a C-arm (a C-arm mechanism) 121 are provided in the X-ray image capturing device 100. Furthermore, the X-ray image capturing device 100 includes various types of control sections (110 to 140), an X-ray generation section 131, an aperture 141, an X-ray image receiving section 150, an analog-to-digital (A/D) conversion section 161, an image processing section 162, a first display section 170, a recording section 180, and a GUI 190. More specifically, the various types of control sections include a system control section 110, a C-arm control section 120, an X-ray control section 130, and an aperture control section 140.

Additionally, the X-ray image receiving section 150 includes an image intensifier 151 and a capturing unit 152. Moreover, the GUI 190 includes a second display section 191 and an input section 192.

The top board 101 is, for example, a board on which the object (a subject person) 200 lies down.

The X-ray generation section 131 and the aperture 141 are provided on one end of the C-arm 121, and the X-ray image receiving section 150 is provided on the other end of the C-arm 121. In other words, the C-arm 121 is configured as a supporting section that supports the X-ray generation section 131 and the aperture 141, and the X-ray image receiving section 150. The C-arm 121 is configured so that the X-ray generation section 131 and the X-ray image receiving section 150 sandwich the object 200 placed on the top board 101 and face each other.

The system control section 110 exercises overall control of operations that are performed in the X-ray image capturing device 100. The system control section 110 controls, as necessary, each section that is provided in the X-ray image capturing device 100.

The C-arm control section 120 is configured as a position control section that controls the position of the C-arm 121 in accordance with control which is performed by the system control section 110. More specifically, the C-arm control section 120 drives the C-arm 121, thereby moving the C-arm 121 to a position at which an image is to be captured on the object 200.

The X-ray generation section 131 includes an X-ray tube that generates X-rays. When the object 200 exists between the X-ray generation section 131 and the X-ray image receiving section 150, the X-ray generation section 131 irradiates the object 200 with X-rays. In other words, the X-ray generation section 131 is configured as a radiation generating section that irradiates the object 200 with radiation. The X-ray control section 130 sends, in accordance with control that is performed by the system control section 110, an X-ray-tube drive signal to the X-ray generation section 131, thereby controlling the X-rays that are emitted from the X-ray generation section 131.

The aperture 141 is provided in front of the X-ray generation section 131 (i.e., between the X-ray generation section 131 and the object 200), and is an X-ray radiation field aperture that adjusts a radiation field of the X-rays which are emitted from the X-ray generation section 131 onto the object 200. In other words, the aperture 141 is configured as a limit section that limits the radiation range of the X-rays which are emitted from the X-ray generation section 131 onto the object 200. The aperture control section 140 performs control of driving the aperture 141 in accordance with control that is performed by the system control section 110. In other words, the aperture control section 140 is configured as a radiation-range control section that controls the radiation range of the X-rays using the aperture 141.

The X-ray image receiving section 150 performs, in accordance with control that is performed by the system control section 110, a process of receiving X-rays that penetrate through the object 200 as an image. More specifically, the image intensifier 151 of the X-ray image receiving section 150 converts a radiolucent image that is formed using X-rays which penetrate through the object 200 into an optical image. The capturing unit 152 of the X-ray image receiving section 150 is configured, for example, using a TV camera or the like. The capturing unit 152 is a capturing unit that captures, as an image (image signals) which is formed using (analog) electric signals, the optical image which is supplied from the image intensifier 151.

The A/D conversion section 161 performs, in accordance with control that is performed by the system control section 110, a process of converting the analog image signals that are output from the capturing unit 152 into digital image signals.

The image processing section 162 performs, in accordance with control that is performed by the system control section 110, image processing, such as changing of contrast or gamma characteristics, on the digital image signals that are output from the A/D conversion section 161, thereby obtaining image data. The image processing section 162 outputs the image data.

The first display section 170 displays an image on the basis of the image data that is output from the image processing section 162. In this case, for example, the first display section 170 displays a captured image that is a moving image of the object 200 which is captured by the capturing unit 152. Furthermore, the first display section 170 displays, as necessary, an image that is reproduced on the basis of image data which is recorded in the recording section 180 (for example, image data of the moving image that is captured by the capturing unit 152).

In the recording section 180, image data of a still image that is extracted while images of the object 200 are being captured is recorded (stored). In this case, regarding a process of extracting a still image to be recorded in the recording section 180, a configuration may be used, in which the process is performed by the image processing section 162. Alternatively, a configuration may be used, in which the process is performed by the system control section 110. Herein, in the first embodiment, the configuration in which the process is performed by the system control section 110 is used as one example. Furthermore, in the recording section 180, as necessary, the image data of the captured image (the moving image) which has been subjected to image processing by the image processing section 162 or various types of information that is used for processes which are performed by the system control section 110 are recorded.

The GUI 190 displays information for a user and so forth on the second display section 191, and is a user interface for inputting, to the system control section 110, an instruction that is provided by the user via the input section 192 which is an input section.

In the first embodiment, the system control section 110 is realized, for example, using the main body of a personal computer (PC) and using application software that operates on the PC. For example, the system control section 110 receives image data of a still image that is recorded in the recording section 180 and that was extracted from a moving image. The system control section 110 performs detection of a marking range and superimposing of marks on the still image, which are described below. The system control section 110 displays the still image with the marks on the second display section 191. Furthermore, the system control section 110 generates operation commands in accordance with input contents that are input to the input section 192, and sends the operation commands to the C-arm control section 120 and the aperture control section 140. In addition, for example, the system control section 110 sends an X-ray radiation signal to the X-ray control section 130 so that the X-ray control section 130 generates the X-ray-tube drive signal. The input section 192 is configured, for example, using a mouse, a keyboard, or a touch panel, and is used to provide an instruction for marking and to perform various types of operations using buttons.

Next, a procedure in a method for driving the X-ray image capturing device 100 shown in FIG. 1 will be described.

Figure 2:
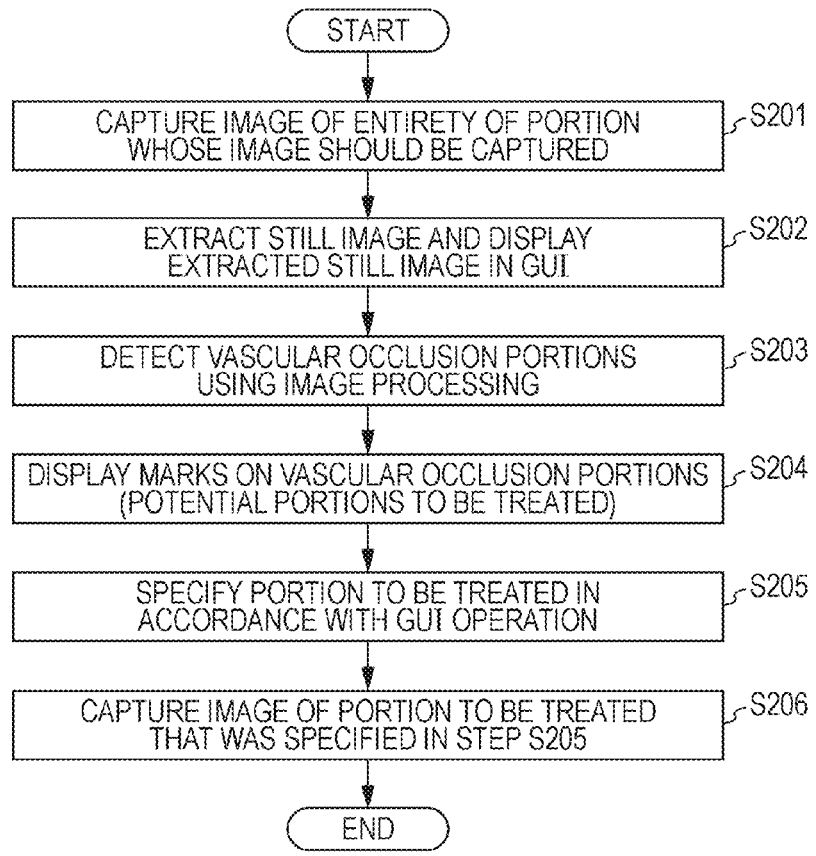
FIG. 2 is a flowchart showing an example of a procedure in a method for driving the X-ray image capturing device (the radiographic image capturing device) according to the first embodiment of the present invention.

FIG. 2 is a flowchart showing an example of the procedure in the method for driving the X-ray image capturing device (the radiographic image capturing device) according to the first embodiment of the present invention. Note that an example in which a blood vessel of the object 200 is applied as an object whose image is to be captured by the capturing unit 152 is described with reference to the flowchart shown in FIG. 2.

Step S201

In step S201, the system control section 110 performs, for example, in accordance with information that is input from the input section 192 or the like, control of capturing an image of the entirety of a portion, whose image should be captured, of the object 200 in order to specify portions, which are to be treated, of the object 200 (i.e., portions, which are to be subjected to surgery, of the object 200).

More specifically, first, the system control section 110 performs control of driving the C-arm 121 so that an image of the entirety of a portion (for example, the heart), whose image should be captured, of the object 200 can be captured. In addition, the system control section 110 performs control of driving the aperture 141 to adjust the radiation field of X-rays, and starts image capturing. After that, the system control section 110 continues image capturing, so that the system control section 110 captures a moving image of the entirety of the portion, whose image should be captured, of the object 200. For example, when a contrast medium is injected into the blood vessel of the object 200 via a catheter in a state in which X-rays are emitted from the X-ray generation section 131 onto the object 200, a fluoroscopic image (an X-ray image) showing a state in which the contrast medium is flowing in the blood vessel is displayed on the first display section 170 in real time.

Figure 3:
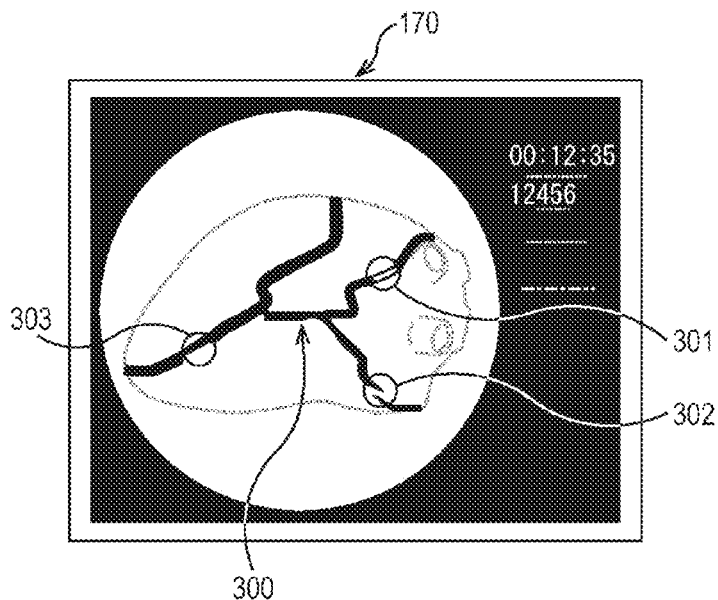
FIG. 3 is an illustration showing an example of a fluoroscopic image (a radiographic image) that is obtained by capturing which is performed in step S201 shown in FIG. 2.

FIG. 3 is an illustration showing an example of the fluoroscopic image (the X-ray image) that is obtained by capturing which is performed in step S201 shown in FIG. 2. Herein, FIG. 3 shows a display screen of the first display section 170.

In the X-ray image shown in FIG. 3, for example, a state of the entirety of the portion (in this example, the heart), whose image should be captured, of the object 200 is illustrated. Furthermore, in FIG. 3, examples of portions to be treated 301, 302, and 303 of a blood vessel 300 of the heart are shown.

Step S202

Next, in step S202, for example, the system control section 110 performs a process of extracting, in accordance with an instruction that is input to the input section 192 of the GUI 190 by a user (a doctor or the like), one still image from the moving image that was captured in step S201.

Figure 4:
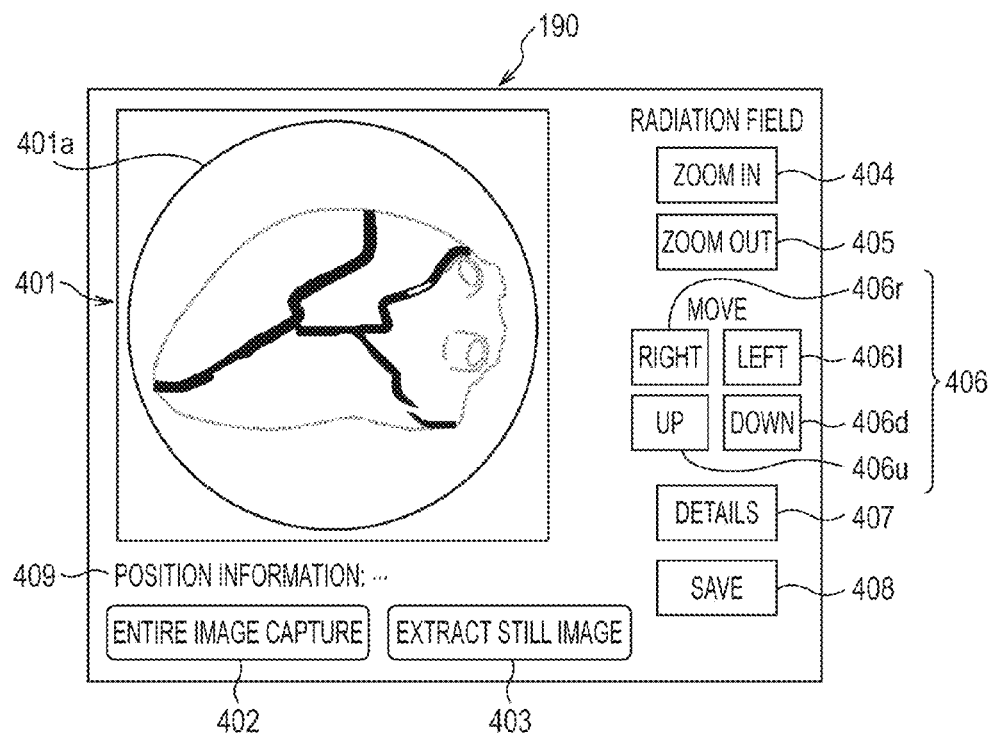
FIG. 4 is an illustration showing an example of a graphical user interface (GUI) that is used in the X-ray image capturing device (the radiographic image capturing device) according to the first embodiment of the present invention.

More specifically, in the first embodiment, the user selects, by operating a button (a still-image extraction button 403 that is shown in FIG. 4 described below) of the GUI 190 in a state in which the contrast medium extends into the blood vessel of the heart, an image frame with which vascular occlusion portions can be most easily detected. In this case, the system control section 110 extracts, in accordance with a selection operation that is performed by the user, a still image with which vascular occlusion portions can be easily detected. The system control section 110 that performs the above-mentioned extraction process is configured as an extraction section. The system control section 110 performs control of displaying the extracted still image on the second display section 191 of the GUI 190. The system control section 110 that performs control of displaying the extracted still image as mentioned above is configured as a still-image display control section.

The details of the above-mentioned process of step S202 will be described below.

FIG. 4 is a schematic illustration showing an example of the GUI 190 that is used in the X-ray image capturing device (the radiographic image capturing device) according to the first embodiment of the present invention. Herein, FIG. 4 shows a display screen of the second display section 191.

A display region 401 shown in FIG. 4 is a region in which a still image 401a that was extracted in step S202 is displayed. Furthermore, various types of buttons (402 to 408) shown in FIG. 4 each correspond to the input section 192 of the GUI 190, and are configured using touch panels in the present example. More specifically, in the example shown in FIG. 4, the various types of buttons include an entire image capture button 402, a still-image extraction button 403, a zoom-in button 404, a zoom-out button 405, a move button 406, a details button 407, and a save button 408. Furthermore, the move button 406 includes a move-right button 406r, a move-left button 406l, a move-up button 406u, and a move-down button 406d.

When the still-image extraction button 403 is selected by the user, the system control section 110 performs a process of sending an instruction to the image processing section 162, and of extracting, as a still image, an image frame that is displayed on the first display section 170 at a point in time in which the still-image extraction button 403 is selected. Simultaneously, the system control section 110 obtains, from the C-arm control section 120, position information that was obtained at a point in time in which the extracted still image was captured, and displays the position information together with the extracted still image in the GUI 190. More specifically, in FIG. 4, an example is shown, in which the extracted still image 401a is displayed in the display region 401, and in which the obtained position information is displayed as position information 409.

In the above-described example, a configuration is described, in which a still image is extracted through a user operation in which the GUI 190 is operated by the user while a moving image of the object 200 is being captured. However, in the first embodiment, the configuration is not limited thereto. For example, a configuration may be used, in which, after capturing of a moving image finishes in order to specify portions, which are to be treated, of the object 200 (portions, which are to be subjected to surgery, of the object 200), the moving image (image data) that is stored in the recording section 180 is reproduced on the first display section 170, and in which an image that is selected through a manual operation by the user (the doctor or the like) is extracted from the moving image. In this case, the image (which is a still image) that is selected by the user through the manual operation using the GUI 190 is displayed in the GUI 190.

Step S203

Next, in step S203, for example, the system control section 110 performs a process of detecting, on the basis of a result of image processing performed by the image processing section 162, vascular occlusion portions from the still image that was extracted in step S202. The details of the process of step S203 will be described below.

Figure 5:
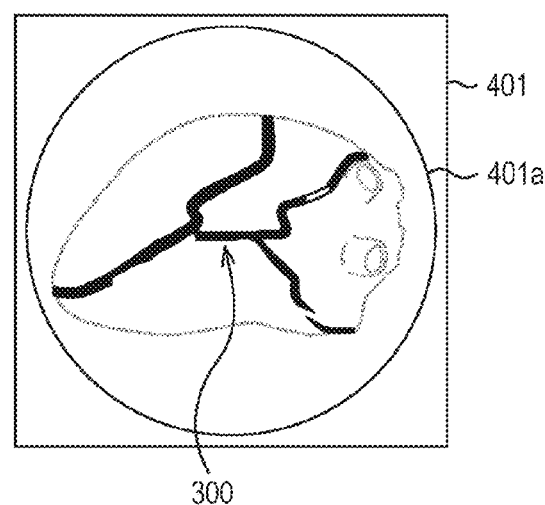
FIG. 5 is an illustration showing a still image that is displayed in a display region shown in FIG. 4.

FIG. 5 is a schematic illustration showing the still image 401a that is displayed in the display region 401 shown in FIG. 4. A state of the blood vessel 300 into which the contrast medium is injected is illustrated in the still image 401a shown in FIG. 5. Herein, because the tone of a portion of the still image 401a corresponding to the blood vessel 300 into which the contrast medium is injected becomes high, pixels having tones that are equal to or higher than a fixed reference value are extracted, whereby an angiogram of the blood vessel 300 can be generated.

Figure 6:
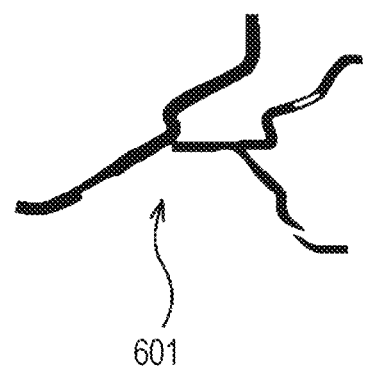
FIG. 6 is an illustration showing an example of binarized data that is obtained by performing a binarization process on an angiogram of a blood vessel shown in FIG. 5.

Next, a binarization process is performed on the angiogram of the blood vessel 300 to obtain binarized data. FIG. 6 is a schematic illustration showing an example of binarized data 601 that is obtained by performing the binarization process on the angiogram of the blood vessel 300 shown in FIG. 5.

Figure 7:
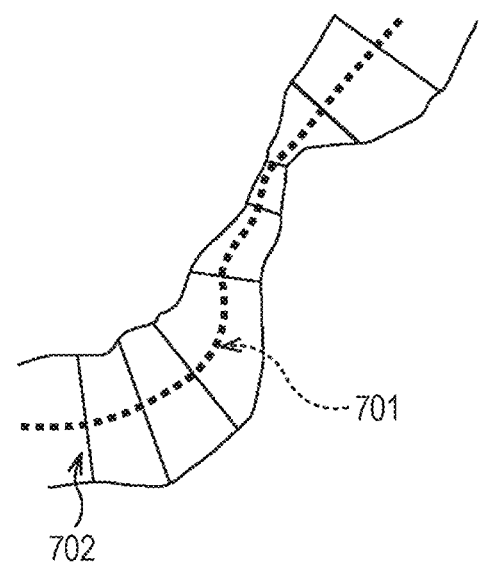
FIG. 7 is an illustration showing an example in which a thinning process is performed on the binarized data shown in FIG. 6.

Next, a thinning process is performed on the binarized data 601. FIG. 7 is a schematic illustration showing an example in which the thinning process is performed on the binarized data 601 shown in FIG. 6. A centerline 701 shown in FIG. 7 is calculated with the thinning process. After that, width vectors that are perpendicular to the centerline 701 are calculated, and width-vector lengths (hn) 702 are calculated at fixed spacings.

Figure 8:
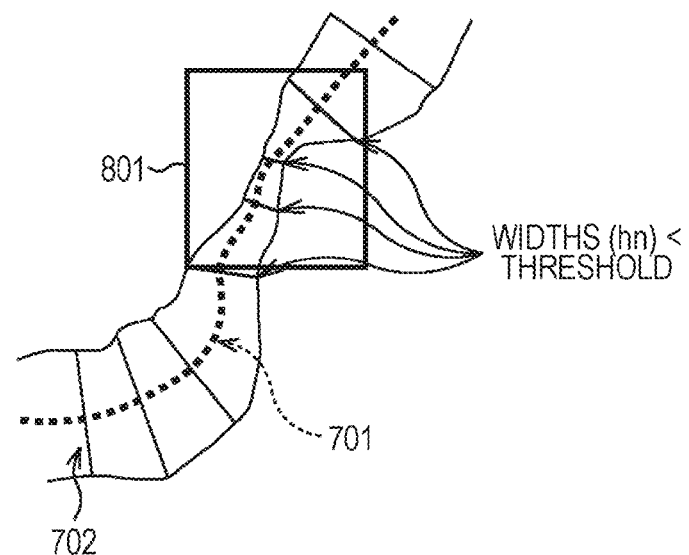
FIG. 8 is an illustration showing an example in which width vectors whose lengths are equal to or narrower than a threshold are calculated using width-vector lengths (hn) shown in FIG. 7.

Next, each of the width-vector lengths (hn) 702 is compared with a threshold, and the width vectors whose lengths are equal to or narrower than the threshold are calculated. FIG. 8 is a schematic illustration showing an example in which the width vectors whose lengths are equal to or narrower than the threshold are calculated using the width-vector lengths (hn) 702 shown in FIG. 7. An extracted region 801 shown in FIG. 8 is extracted using vector coordinates of the width vectors whose lengths are equal to or narrower than the threshold and which have been calculated in this manner, and the extracted region 801 is considered as a vascular occlusion portion (a potential portion to be treated).

Figure 9:
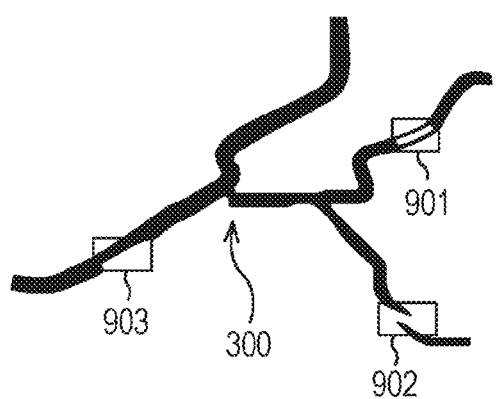
FIG. 9 is a schematic illustration showing an example of vascular occlusion portions that are detected from the angiogram of the blood vessel shown in FIG. 5.

FIG. 9 is a schematic illustration showing examples of vascular occlusion portions that are detected from the angiogram of the blood vessel 300 shown in FIG. 5. A group of width vectors whose lengths are equal to or narrower than the threshold is calculated along the angiogram of the blood vessel 300 with the above-described process, whereby vascular occlusion portions 901, 902, and 903 shown in FIG. 9 can be extracted.

Step S204

Next, in step S204, the system control section 110 performs control of displaying marks on the vascular occlusion portions that were detected in step S203 for the still image that was displayed in step S202. The system control section 110 that performs control of displaying marks as mentioned above is configured as a mark display control section. In this case, the system control section 110 also performs a process of recording attribute information concerning the displayed marks as an attribute information table, for example, in the recording section 180. The details of the process of step S204 will be described below.

Figure 10:
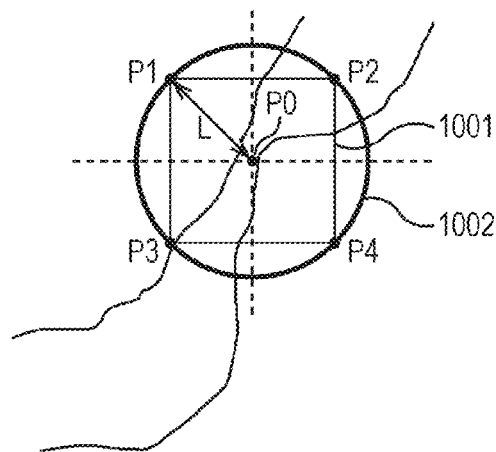
FIG. 10 is an illustration showing an example of a method for superimposing a mark on a still image that is displayed in step S202 shown in FIG. 2.

FIG. 10 is a schematic illustration showing an example of a method for superimposing a mark on the still image 401a that was displayed in step S202 shown in FIG. 2.

A vascular occlusion portion 1001 shown in FIG. 10 is displayed as a rectangular region defined using P1 (Xp1, Yp1), P2 (Xp2, Yp2), P3 (Xp3, Yp3), and P4 (Xp4, Yp4). When the center point of the rectangular region that corresponds to the vascular occlusion portion 1001 is defined as P0 (Xp0, Yp0), a mark 1002 is displayed as a graphics frame having the central point P0 serving as a center and a radius (distance) of L. In the first embodiment, a configuration is used, in which a default shape of the mark 1002 is a circular shape, and in which the mark 1002 can be displayed as an octagonal graphics frame, a rectangular graphics frame, or the like in accordance with the shape of the aperture 141 that is configured, for example, using a collimator.

Figure 11:
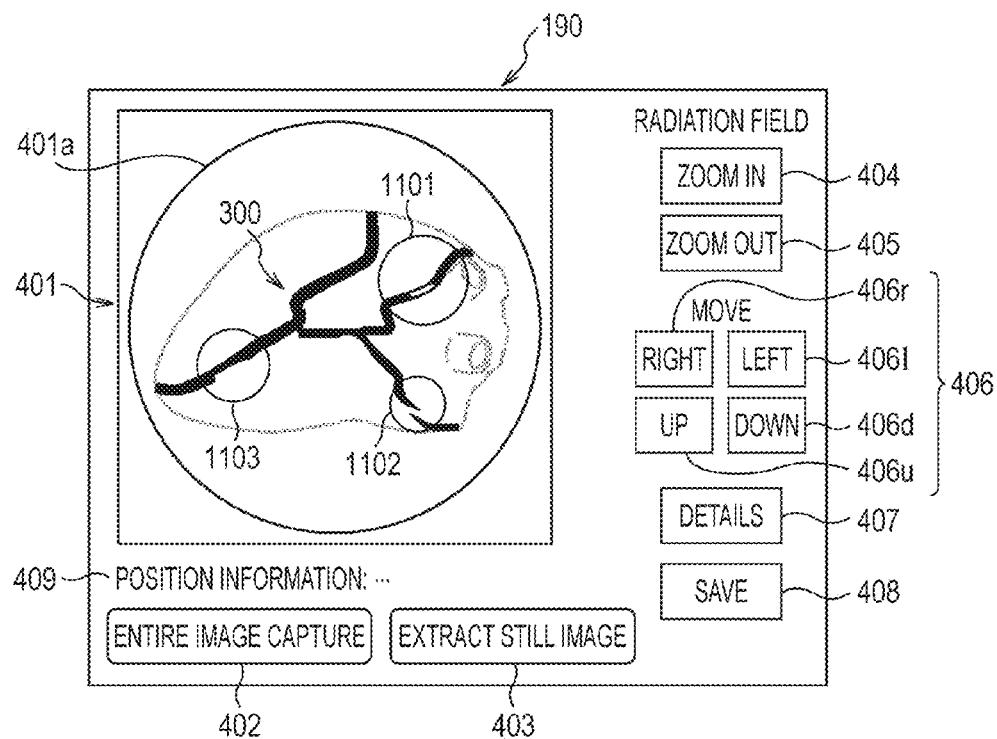
FIG. 11 is an illustration showing an example in which vascular occlusion portions (potential portions to be treated) are marked with marks in the GUI that is used in the X-ray image capturing device (the radiographic image capturing device) according to the first embodiment of the present invention.

FIG. 11 is a schematic illustration showing an example in which vascular occlusion portions (potential portions to be treated) are marked with marks in the GUI 190 that is used in the X-ray image capturing device (the radiographic image capturing device) according to the first embodiment of the present invention. More specifically, in the GUI 190 shown in FIG. 11, an example is shown, in which vascular occlusion portions (potential portions to be treated) that correspond to predetermined portions of the still image 401a are marked with circular marks 1101, 1102, and 1103.

Figures 12, 13:
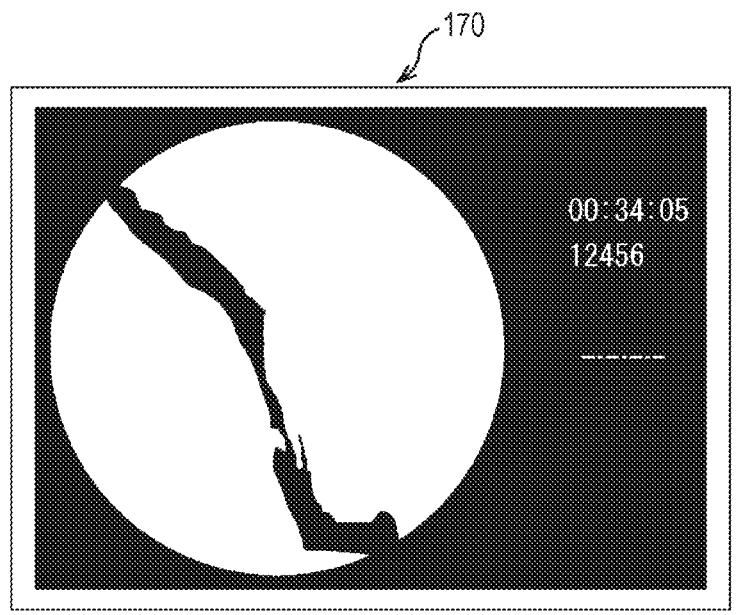
FIG. 12 is an illustration showing an example of an attribute information table concerning marks that are displayed in step S204 shown in FIG. 2.
FIG. 13 is an illustration showing an example of a fluoroscopic image (a radiographic image) that is obtained by capturing which is performed in step S206 shown in FIG. 2.

FIG. 12 is a schematic illustration showing an example of the attribute information table concerning the marks that are displayed in step S204 shown in FIG. 2. As described above, the attribute information table concerning the marks that is shown in FIG. 12 is recorded, for example, in the recording section 180.

Herein, in the attribute information table concerning the marks that is shown in FIG. 12 in the first embodiment, for each mark, a shape of the mark, a color (initial color) of the mark, position information and size information concerning the mark, and so forth are shown in relation to one another. Herein, for example, the central point P0 shown in FIG. 10 can be applied as the position information. For example, the radius (distance) of L shown in FIG. 10 can be applied as the size information. Note that the above-described position information and size information are examples, and a configuration in which other information is used as the position information and size information may be used. Furthermore, in the attribute information table concerning the marks that is shown in FIG. 12, for example, a mark 1 corresponds to the mark 1101 shown in FIG. 11, a mark 2 corresponds to the mark 1102 shown in FIG. 11, and a mark 3 corresponds to the mark 1103 shown in FIG. 11.

Step S205

Next, in step S205, the system control section 110 performs a process of specifying, in accordance with an instruction that is input to the input section 192 of the GUI 190 by the user (the doctor or the like), a portion to be treated. The details of the process of step S205 will be described below.

The marks 1101 to 1103 that were first shown in FIG. 11 on the still image 401a in step S204 are considered as a group of potential portions to be treated. When the user adjusts the position or size of one of the marks through an operation using the GUI 190, the system control section 110 specifies a portion to be treated corresponding to the mark in accordance with the operation. In this case, the mark can be removed, or a mark can be added.

First, when adjustment to the size of a mark is performed so that the mark is enlarged/reduced, the target mark is set to be in an active state by clicking the mouse that is the input section 192, and then, the zoom-in button 404 or the zoom-out button 405 is selected, whereby the mark can be enlarged or reduced. Furthermore, when adjustment to the position of a mark is performed so that the mark is moved, similarly, the mark is set to be in the active state by clicking the mouse, and then, the move button 406 (any one of the move-right button 406r, the move-left button 406l, the move-up button 406u, and the move-down button 406d) is selected, whereby the mark can be moved. In the first embodiment, in addition to using the above-mentioned operation method in which one of the buttons is selected, a mark can be moved and enlarged/reduced by directly dragging and dropping the mark to a target position. Moreover, when displaying of a mark on a new portion to be treated is performed, for example, a portion to be treated is specified on the still image 401a using the mouse or the like, whereby a mark having a predetermined size can be displayed at the position of the specified portion to be treated.

Step S206

Next, in step S206, the system control section 110 performs control of capturing an image used for surgery or treatment, i.e., control of capturing a fluoroscopic image of the portion to be treated that was specified in step S205. The system control section 110 that performs control of capturing an image as mentioned above is configured as a capture control section.

More specifically, when the user selects a region of the predetermined mark by double-clicking the mouse, the system control section 110 starts capturing of a fluoroscopic image of the portion to be treated that is a corresponding portion of the object 200 which corresponds to the region of the predetermined mark. In this case, the system control section 110 reads the position information and the size information concerning the predetermined mark from the attribute information table concerning the marks that is shown in FIG. 12. The system control section 110 sends the position information to the C-arm control section 120, and sends the size information to the aperture control section 140.

When the C-arm control section 120 receives the position information from the system control section 110, the C-arm control section 120 calculates an amount of movement with which the center of the predetermined mark and the center of an optical axis of the capturing unit 152 can coincide with each other. The C-arm control section 120 moves the C-arm 121 by the amount of movement. Furthermore, when the aperture control section 140 receives the size information from the system control section 110, the aperture control section 140 determines an amount of aperture with which the radiation range of X-rays can be set to the minimum range required for capturing the fluoroscopic image. The aperture control section 140 drives the aperture 141 by the amount of aperture.

After alignment of the C-arm 121 and the aperture 141 that is performed by the C-arm control section 120 and the aperture control section 140 is completed, the system control section 110 sends the X-ray radiation signal to the X-ray control section 130. With the X-ray radiation signal, the X-ray-tube drive signal is sent from the X-ray control section 130 to the X-ray generation section 131, and X-rays are emitted from the X-ray generation section 131 onto the object 200.

Furthermore, when the fluoroscopic image (the radiographic image) is captured in step S206, the system control section 110 performs a process of calculating an enlargement ratio of the fluoroscopic image (the radiographic image) from the size information concerning the predetermined mark, and of displaying the captured fluoroscopic image in an enlarged manner in accordance with the calculated enlargement ratio on the first display section 170.

FIG. 13 is an illustration showing an example of the fluoroscopic image (the radiographic image) that is obtained by capturing which is performed in step S206 shown in FIG. 2. Herein, in the fluoroscopic image shown in FIG. 13, the portion to be treated is displayed in an enlarged manner, compared with the portion to be treated that is displayed in the fluoroscopic image shown in FIG. 3. Note that the fluoroscopic image (the radiographic image) shown in FIG. 13 is obtained, for example, in a case in which the predetermined mark is the mark 1102, and in which image capturing is performed at the mark 1102.

Furthermore, when the entire image capture button 402 shown in FIG. 11 is selected by the user, the system control section 110 finishes capturing of an image at the predetermined mark, and performs a process of capturing an image of the entirety of the portion, whose image should be captured, of the object 200 again.

In the X-ray image capturing device 100 according to the first embodiment, a mark is displayed on a predetermined portion, which can correspond to a portion to be subjected to surgery, of a still image that is displayed in the GUI 190, and, when the displayed mark is selected, capturing of an image of a corresponding portion of the object 200 that corresponds to the predetermined portion is performed.

With the above-described configuration, because the position of the portion, which is to be subjected to surgery, of the object 200 can be checked on the still image that is displayed in the GUI 190, the positional relationships between a portion, whose image should be captured, of the object and the portion, which is to be subjected to surgery, of the object can be easily grasped. Additionally, capturing of an image of the corresponding portion of the object 200 that corresponds to the predetermined portion on which the selected mark is displayed is performed. Accordingly, image capturing can be performed by irradiating only the corresponding portion with X-rays. Thus, reduction in dose of X-rays (radiation) with which the object is irradiated can be realized.

Moreover, in the first embodiment, image processing is performed on the still image. A potential portion to be treated is considered as the predetermined portion, and a mark is displayed on the potential portion to be treated. Accordingly, even when a plurality of portions to be treated exist in reality, the plurality of portions to be treated are prevented from being missed, and treatment mistakes can be prevented. Furthermore, because the position and size of the mark can be set through a user operation in which the GUI 190 is operated by the user, the radiation range of X-rays can be set to any range. Thus, a time taken to adjust a position at which an image is to be captured or a time taken to narrow down the radiation range can be reduced when image capturing is performed for treatment, and exposure of the object to unnecessary radiation can be reduced.

Second Embodiment

Next, a second embodiment of the present invention will be described.

A schematic configuration of an X-ray image capturing device (a radiographic image capturing device) according to the second embodiment is the same as that of the X-ray image capturing device 100 according to the first embodiment shown in FIG. 1.

Next, a procedure in a method for driving the X-ray image capturing device 100 according to the second embodiment will be described.

Figure 14:
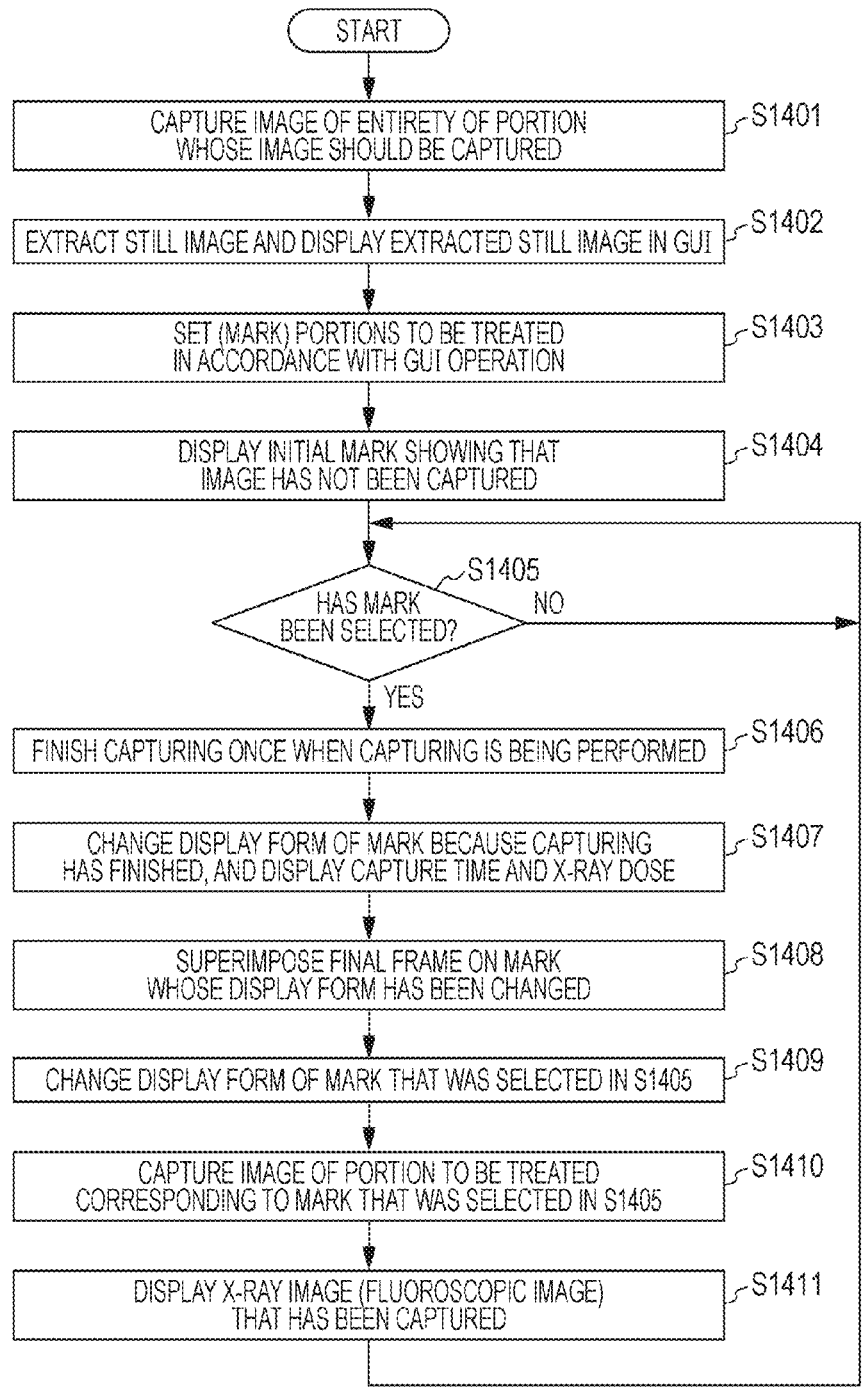
FIG. 14 is a flowchart showing an example of a procedure in a method for driving an X-ray image capturing device (a radiographic image capturing device) according to a second embodiment of the present invention.

FIG. 14 is a flowchart showing an example of the procedure in the method for driving the X-ray image capturing device (the radiographic image capturing device) according to the second embodiment of the present invention. Note that an example in which a blood vessel of the object 200 is applied as an object whose image is to be captured by the capturing unit 152 is described with reference to the flowchart shown in FIG. 14.

Step S1401

In step S1401, the system control section 110 performs, for example, in accordance with information that is input from the input section 192 or the like, control of capturing an image of the entirety of a portion, whose image should be captured, of the object 200, as in step S201.

More specifically, first, the system control section 110 performs control of driving the C-arm 121 so that an image of the entirety of a portion (for example, the heart), whose image should be captured, of the object 200 can be captured. In addition, the system control section 110 performs control of driving the aperture 141 to adjust the radiation field of X-rays, and starts image capturing. After that, the system control section 110 continues image capturing, so that the system control section 110 captures a moving image of the entirety of the portion, whose image should be captured, of the object 200. For example, when a contrast medium is injected into the blood vessel of the object 200 via a catheter in a state in which X-rays are emitted from the X-ray generation section 131 onto the object 200, a fluoroscopic image (a radiographic image) showing a state in which the contrast medium is flowing in the blood vessel is displayed on the first display section 170 in real time. In other words, a fluoroscopic image (a radiographic image) of the entire heart that includes the portions to be treated 301, 302, and 303 shown in FIG. 3 is displayed on the first display section 170.

Step S1402

Next, in step S1402, for example, the system control section 110 performs a process of extracting, in accordance with an instruction that is input to the input section 192 of the GUI 190 by a user (a doctor or the like), one still image from the moving image that was captured in step S1401. The system control section 110 that performs the above-mentioned extraction process is configured as an extraction section. The system control section 110 performs control of displaying the extracted still image on the second display section 191 of the GUI 190. The system control section 110 that performs control of displaying the extracted still image as mentioned above is configured as a still-image display control section. In the second embodiment, a case is described, in which an image frame including the clearest image of affected portions is extracted from the fluoroscopic image (the radiographic image) of the entire heart as a still image, and in which the still image is displayed in the GUI 190.

Figure 15:
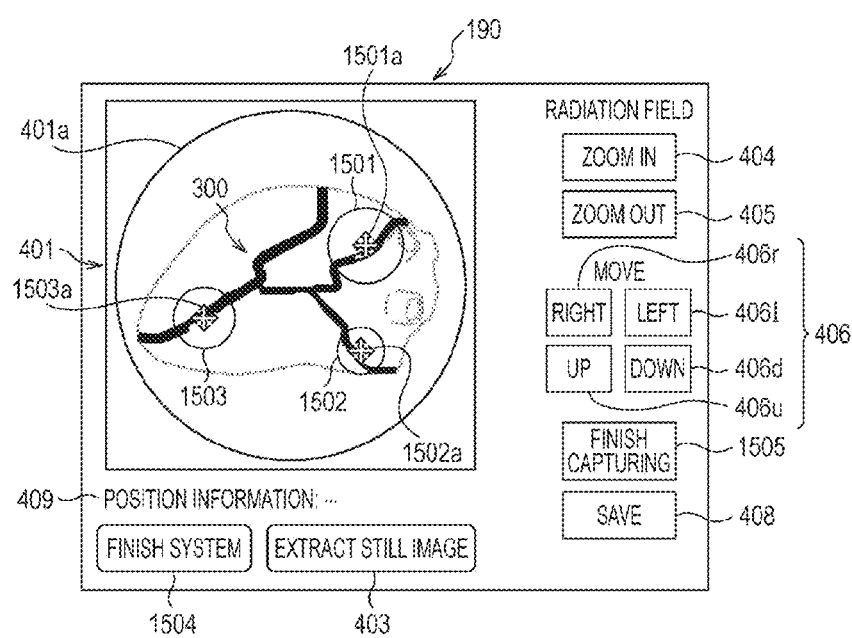
FIG. 15 is an illustration showing an example of a GUI that is used in the X-ray image capturing device (the radiographic image capturing device) according to the second embodiment of the present invention.

More specifically, in the second embodiment, the user selects, by operating a button (the still-image extraction button 403 that is shown in FIG. 15 described below) of the GUI 190 in a state in which the contrast medium extends into the blood vessel of the heart, an image frame with which affected portions that are required to be treated can be most easily detected. In this case, the system control section 110 extracts, in accordance with a selection operation that is performed by the user, a still image with which affected portions that are required to be treated can be easily detected. The system control section 110 performs a process of displaying the extracted still image on the second display section 191 of the GUI 190. The details of the process of step S1402 will be described below.

FIG. 15 is a schematic illustration showing an example of the GUI 190 that is used in the X-ray image capturing device (the radiographic image capturing device) according to the second embodiment of the present invention. Herein, FIG. 15 shows the display screen of the second display section 191. Furthermore, elements shown in FIG. 15 that are the same as elements shown in FIG. 11 are denoted by the same reference numerals. Herein, in the GUI 190 shown in FIG. 15, a system finish button 1504 is provided instead of the entire image capture button 402 shown in FIG. 11, and a capture finish button 1505 is provided instead of the details button 407.

When the still-image extraction button 403 is selected by the user, the system control section 110 performs a process of sending an instruction to the image processing section 162, and of extracting, as a still image, an image frame that is displayed on the first display section 170 at a point in time in which the still-image extraction button 403 is selected. Simultaneously, the system control section 110 obtains, from the C-arm control section 120, position information that was obtained at a point in time in which the extracted still image was captured, and displays the position information together with the extracted still image in the GUI 190. More specifically, in FIG. 15, an example is shown, in which the extracted still image 401*a* is displayed in the display region 401, and in which the obtained position information is displayed as the position information 409.

In the above-described example, a configuration is described, in which a still image is extracted through a user operation in which the GUI 190 is operated by the user while a moving image of the object 200 is being captured. However, in the second embodiment, the configuration is not limited thereto. For example, a configuration may be used, in which, after capturing of a moving image finishes in order to specify portions, which are to be treated, of the object 200 (portions, which are to be subjected to surgery, of the object 200), the moving image (image data) that is stored in the recording section 180 is reproduced on the first display section 170, and in which an image that is selected through a manual operation by the user (the doctor or the like) is extracted from the moving image. In this case, the image (which is a still image) that is selected by the user through the manual operation using the GUI 190 is displayed in the GUI 190.

Step S1403

Next, in step S1403, the system control section 110 performs a process of setting (marking), in accordance with an instruction that is input to the GUI 190 by the user (the doctor or the like), portions which seem to be required to be treated or whose images seem to be required to be captured, i.e., portions to be treated, on the still image 401a shown in FIG. 15.

More specifically, when the user inputs coordinates that are located in the still image 401a using the input section 192 such as a mouse or a touch panel, the system control section 110 marks portions to be treated 1501a, 1502a, and 1503a shown in FIG. 15 on the still image 401a in accordance with the input coordinates.

Herein, each of the portions to be treated 1501a, 1502a, and 1503a corresponds to coordinates that are input through an instruction provided by the user.

Step S1404

Next, in step S1404, the system control section 110 performs control of displaying initial marks, each of which indicates that an image has not been captured, on the still image 401 so that the center of each of the initial marks is positioned at coordinates that correspond to a corresponding one of the portions to be treated that were set (marked) in step S1403 and the initial mark has a predetermined size. The system control section 110 that performs control of displaying marks as mentioned above is configured as a mark display control section. In this case, the system control section 110 also performs a process of recording attribute information concerning the displayed marks as an attribute information table, for example, in the recording section 180. The attribute information table concerning the marks will be described below.

In FIG. 15, initial marks 1501 to 1503 are displayed so that the center of each of the initial marks 1501 to 1503 is positioned at coordinates that correspond to a corresponding one of the portions to be treated 1501a, 1502a, and 1503a and each of the initial marks 1501 to 1503 is formed as a (red) circular graphics frame indicating that an image has not been captured (indicating that treatment has not been performed). Furthermore, when the user (the doctor or the like) operates the zoom-in button 404, the zoom-out button 405, the move button 406, or the like of the GUI 190 in accordance with the size of each of the portions to be treated, whereby the position and size of a corresponding one of the initial marks can be changed. Herein, a method in which an initial mark is displayed in a predetermined size is described. However, for example, when the user provides an instruction for specifying a portion to be treated using the mouse or the like, the user may input coordinates of two points, i.e., coordinates of upper-left and lower-right points, so that the two points surround an affected portion to obtain a rectangular region defined using the two points, and may set the size of a mark so that the mark includes the obtained rectangular region.

Step S1405

Next, in step S1405, the system control section 110 determines whether or not one of the marks that were displayed in the GUI 190 has been selected by the user. Herein, for example, the user can select any one of the marks by double-clicking the mouse or the like that is the input section 192. Furthermore, any one of the marks can be selected not only by double-clicking the mouse but also via a different input device such as a touch panel.

Herein, the attribute information table concerning the marks that were displayed in step S1404 shown in FIG. 14 will be described.

Figure 16:
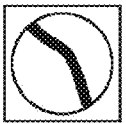
FIG. 16 is an illustration showing an example of an attribute information table concerning marks that are displayed in step S1404 shown in FIG. 14.

FIG. 16 is a schematic illustration showing an example of the attribute information table concerning the marks that were displayed in step S1404 shown in FIG. 14. As described above, the attribute information table concerning the marks that is shown in FIG. 16 is recorded, for example, in the recording section 180.

Herein, in the attribute information table concerning the marks that is shown in FIG. 16 in the second embodiment, for each mark, a mark identification (ID), position information and size information concerning the mark, a capture state, a capture time, a dose of X-rays, a final frame including a captured image, and so forth are shown in relation to one another. For example, when the GUI 190 is operated by the user, the system control section 110 searches, in accordance with the position information that is listed in the attribute information table concerning the marks that is shown in FIG. 16, a mark region in which coordinates of a mark selected by double-clicking the mouse are located, thereby specifying the selected mark. Furthermore, in the attribute information table concerning the marks that is shown in FIG. 16, for example, a mark having a mark ID of MK001 corresponds to the mark 1501 shown in FIG. 15, a mark having a mark ID of MK002 corresponds to the mark 1502 shown in FIG. 15, and a mark having a mark ID of MK003 corresponds to the mark 1503 shown in FIG. 15.

Figure 17:
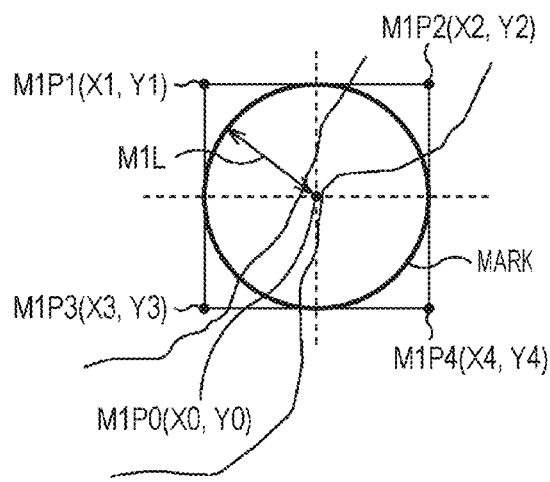
FIG. 17 is an illustration showing an example of position information and size information that are listed in the attribute information table concerning marks that is shown in FIG. 16.

FIG. 17 is a schematic illustration showing an example of the position information and the size information that are listed in the attribute information table concerning the marks which is shown in FIG. 16. In FIG. 17, a case in which the mark having a mark ID of MK001 shown in FIG. 16 is displayed is illustrated.

For example, regarding the mark having a mark ID of MK001 shown in FIG. 16, a region that is surrounded by four points, i.e., M1P1, M1P2, M1P3, and M1P4, is defined as the position information concerning the mark. Furthermore, a circle is defined so that the center of the circle is M1P0 which is the center of the region, and a radius M1L of the circle is defined as the size information concerning the mark. Accordingly, for example, supposing that coordinates which are selected by the user by double-clicking the mouse is IN(X,Y), whether or not IN (X, Y) is located in a region of the mark having a mark ID of MK001 can be determined. When IN (X, Y) is located in the region of the mark having a mark ID of MK001, the system control section 110 further determines that the mark having a mark ID of MK001 has been selected.

As a result of determination in step S1405, when none of the marks displayed in the GUI 190 has been selected, the system control section 110 waits in step S1405 until one of the marks displayed in the GUI 190 is selected. In contrast, as a result of determination in step S1405, when one of the marks displayed in the GUI 190 has been selected, the system control section 110 proceeds to step S1406.

Step S1406

When the system control section 110 proceeds to step S1406, the system control section 110 performs a process of terminating image capturing that has been performed. Note that, in the process of terminating image capturing in step S1406, not only a process of terminating capturing of an image of the entirety of the portion, whose image should be captured, of the object 200, which was performed in step S1401, but also a process of terminating capturing of an image of the portion, which is to be treated, of the object 200, which was performed in a loop including steps S1405 to S1411, is performed. Furthermore, image capturing can be terminated in step S1406 in response to a user operation in which the capture finish button 1505 that is provided in the GUI 190 shown in FIG. 15 is operated by the user.

Step S1407

In step S1407, first, the system control section 110 searches, in response to performance of the process of terminating image capturing in step S1406, the attribute information table concerning the marks that is shown in FIG. 16 for a mark whose capture state is in a mode of "being captured". When a mark whose capture state is in the mode of "being captured" exists, the system control section 110 changes the capture state of the mark in the attribute information table concerning the marks that is shown in FIG. 16 to a mode of "captured", and changes a display form of the mark to a display form indicating that an image has been "captured" in the GUI 190. Furthermore, the system control section 110 records, as information concerning the mark in the attribute information table concerning the marks that is shown in FIG. 16, a capture time taken to capture an image in the region of the mark and a dose of X-rays that are emitted in the capture time. Additionally, the system control section 110 displays the information concerning the mark at a predetermined position that is calculated on the basis of the position information concerning the mark in the GUI 190.

Figure 18:
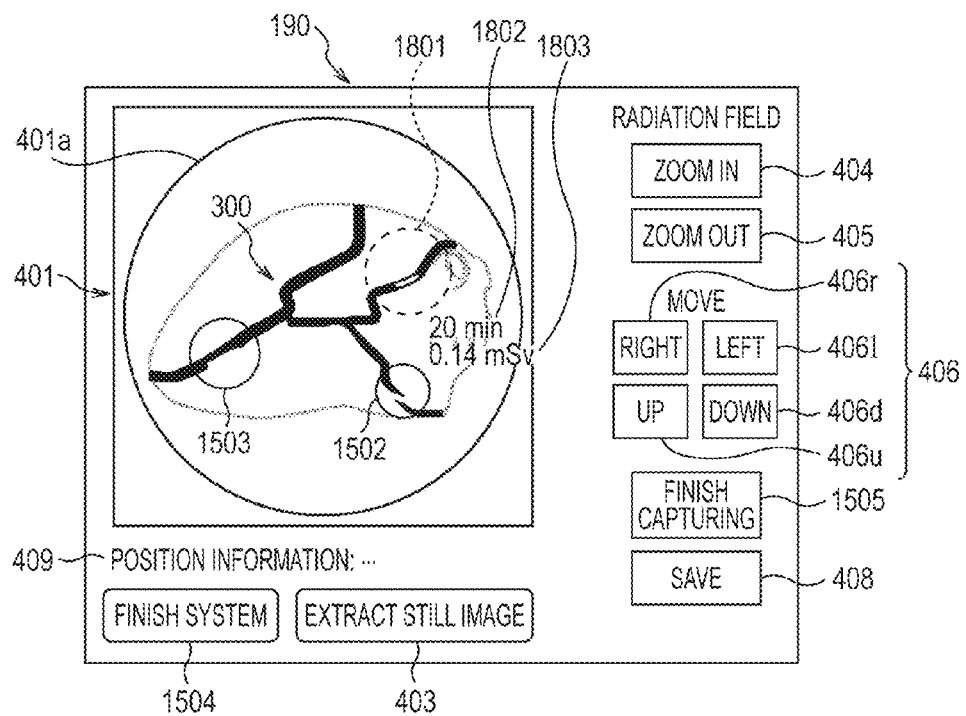
FIG. 18 is an illustration showing an example of the GUI after a process of step S1407 shown in FIG. 14 is performed.

FIG. 18 is a schematic illustration showing an example of the GUI 190 after the process of step S1407 shown in FIG. 14 is performed.

In the example shown in FIG. 18, a case is illustrated, in which image capturing has finished at the mark 1501 shown in FIG. 15 (the mark having a mark ID of MK001 shown in FIG. 16). The mark 1501 has been changed to a mark 1801 indicating that an image has been captured, and the mark 1801 is displayed. More specifically, the mark 1501 was displayed as a graphics frame with a (red) solid line indicating that an image has not been captured (indicating that treatment has not been performed). However, because image capturing has finished at the mark 1501, the mark 1501 has been changed to the mark 1801 that is displayed as a graphics frame with a (blue) dotted line indicating that an image has been captured. Furthermore, the system control section 110 performs control of displaying the capture time and the dose of X-rays, which were recorded in the attribute information table concerning the marks that is shown in FIG. 16, as capture-time information 1802 and X-ray dose information 1803, respectively, in the GUI 190. The system control section 110 that performs control of displaying capture-time information and X-ray dose information as mentioned above is configured as an information display control section. In this case, because a state of an affected portion is displayed in the mark 1801, the system control section 110 displays the capture-time information 1802 and the X-ray dose information 1803 at the lower-right side of the mark 1801 in relation to the mark 1801 so that the capture-time information 1802 and the X-ray dose information 1803 do not cover the inside of the mark 1801.

Step S1408

Next, in step S1408, first, the system control section 110 saves, in the attribution information table concerning the marks that is shown in FIG. 16, a final frame of the moving image. Capturing of the moving image finished in step S1406. Furthermore, the system control section 110 reduces the size of the final frame in accordance with the size of the mark whose display form was changed in the step S1407, and superimposes the final frame on the region of the mark on the still image 401a in the GUI 190 as a mask image. The system control section 110 that performs the above-mentioned superimposing process is configured as a superimposing section. For example, the final frame that is listed in the attribution information table concerning the marks which is shown in FIG. 16 is displayed in a reduced manner in a region of the mark 1801 shown in FIG. 18. In this manner, the final frame (after treatment is performed) is superimposed on the still image 401a, whereby a state of a portion corresponding to the mark after treatment is performed can be checked.

Step S1409

Next, in step S1409, the system control section 110 performs a process of changing the display form of the (one) mark that was selected in step S1405.

Figure 19:
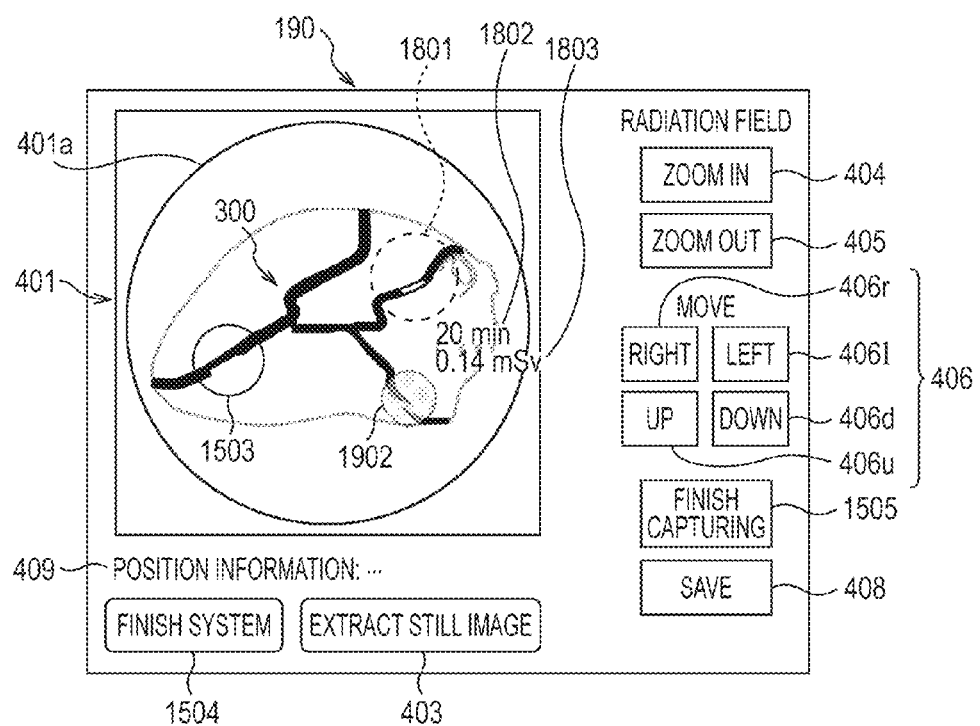
FIG. 19 is an illustration showing an example of the GUI after a process of step S1409 shown in FIG. 14 is performed.

FIG. 19 is a schematic illustration showing an example of the GUI 190 after the process of step S1409 shown in FIG. 14 is performed.

In the example shown in FIG. 19, a case is illustrated, in which the mark 1502 shown in FIG. 18 (the mark having a mark ID of MK002 shown in FIG. 16) is selected in step S1405. The mark 1502 has been changed to a mark 1902 indicating that an image is being captured, and the mark 1902 is displayed. More specifically, the mark 1502 was displayed as a graphics frame with a (red) solid line indicating that an image has not been captured (indicating that treatment has not been performed). However, the mark 1902 is displayed as a graphics frame, the inside of which is filled with a (red) color indicating that an image is being captured. In this case, the system control section 110 changes the capture state of the mark (having a mark ID of MK002) to the mode of "being captured" in the attribute information table concerning the marks which is shown in FIG. 16.

Step S1410

Next, in step S1410, the system control section 110 performs control of capturing a fluoroscopic image (a radiographic image) of a portion to be treated that is a corresponding portion of the object 200 which corresponds to the mark selected in step S1405. The system control section 110 that performs control of capturing an image as mentioned above is configured as a capture control section. Note that, although image capturing starts in response to selection of a mark in step S1405, in addition, a configuration may be used, in which image capturing starts, for example, in response to a user operation in which a foot pedal (that is the input section 192) is pressed by the user.

More specifically, first, the system control section 110 reads, from the attribute information table shown in FIG. 16, position information and size information concerning the mark (having a mark ID of MK002) that was selected in step S1405. The system control section 110 sends the position information to the C-arm control section 120, and sends the size information to the aperture control section 140.

When the C-arm control section 120 receives the position information from the system control section 110, the C-arm control section 120 calculates, from the position information, an amount of movement with which the center of the mark and the center of the optical axis of the capturing unit 152 can coincide with each other. The C-arm control section 120 moves the C-arm 121 by the amount of movement. Furthermore, when the aperture control section 140 receives the size information from the system control section 110, the aperture control section 140 determines, from the size information, an amount of aperture with which the radiation range of X-rays can be set to the minimum range required for capturing the fluoroscopic image. The aperture control section 140 drives the aperture 141 by the amount of aperture. After alignment of the C-arm 121 and the aperture 141 that is performed by the C-arm control section 120 and the aperture control section 140 is completed, the system control section 110 sends the X-ray radiation signal to the X-ray control section 130. With the X-ray radiation signal, the X-ray-tube drive signal is sent from the X-ray control section 130 to the X-ray generation section 131, and X-rays are emitted from the X-ray generation section 131 onto the object 200.

Step S1411

Next, in step S1411, the system control section 110 performs a process of calculating an enlargement ratio of the fluoroscopic image (the radiographic image) from the size information concerning the mark that was selected in step S1405, and of displaying the captured fluoroscopic image in an enlarged manner in accordance with the calculated enlargement ratio on the first display section 170.

Figure 20:
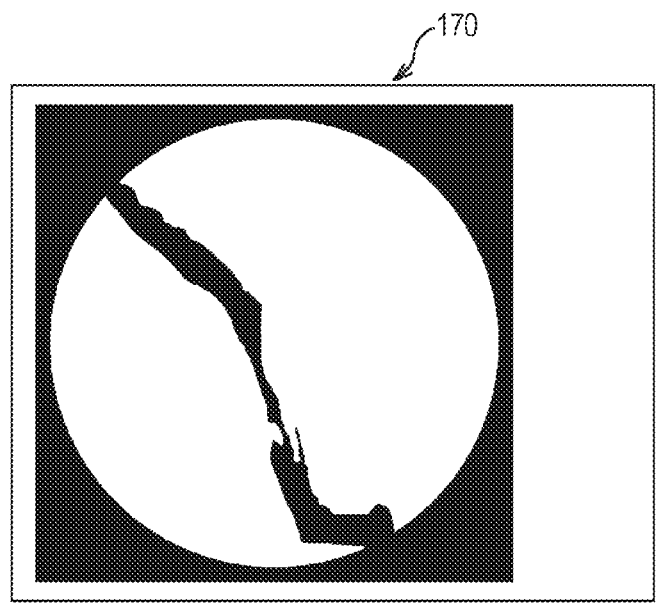
FIG. 20 is an illustration showing an example of a fluoroscopic image (a radiographic image) that is displayed by performing a display process of step S1411 shown in FIG. 14.

FIG. 20 is an illustration showing an example of the fluoroscopic image (the radiographic image) that is displayed by performing the display process of step S1411 shown in FIG. 14. Herein, in the fluoroscopic image shown in FIG. 20, the portion to be treated is displayed in an enlarged manner, compared with the portion to be treated that is displayed in the fluoroscopic image shown in FIG. 3.

When the process of step S1411 finishes, the system control section 110 returns to step S1405, and the processes onward from step S1405 are performed again.

Figure 21:
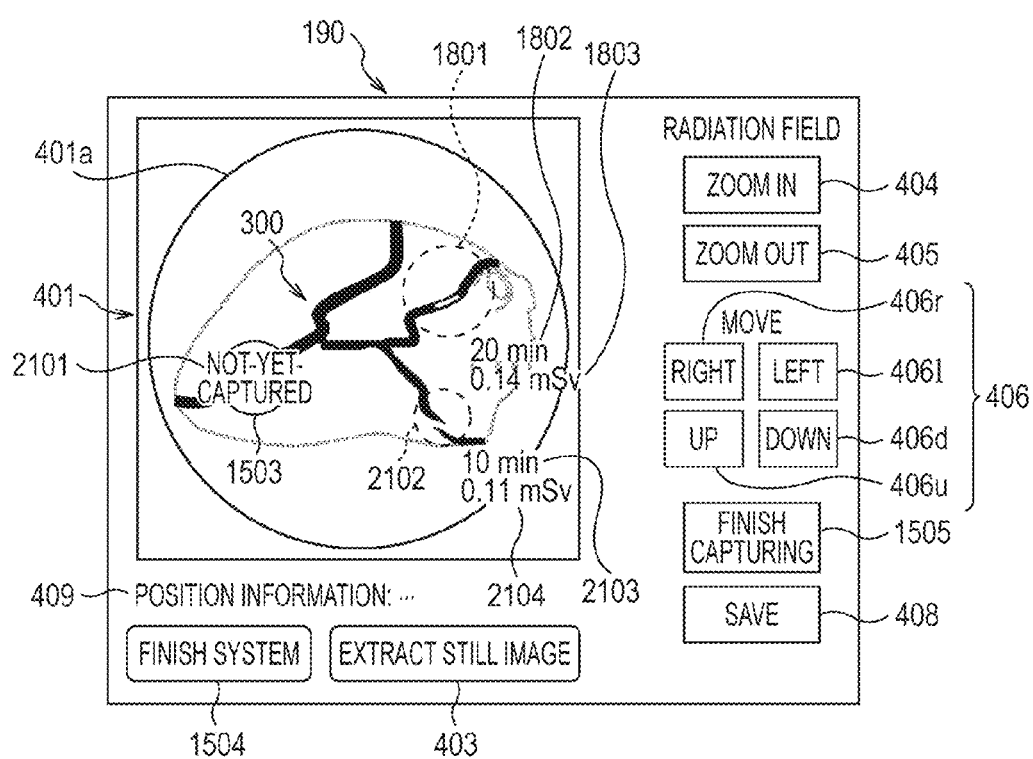
FIG. 21 is an illustration showing an example of the GUI in a case in which a system finish button shown in FIG. 19 is operated.

Furthermore, when capturing of an image of the portion to be treated that corresponds to the mark 1902 finishes when the GUI 190 is in a state shown in FIG. 19, the mark 1902 is changed to a display form (a graphics frame with a (blue) dotted line) indicating that an image has been "captured", which is shown as a mark 2102 in FIG. 21. Moreover, as in the case of the mark 1801, capture-time information 2103 and X-ray dose information 2104 are displayed at the lower-right side of the mark 2102. In this case, the capture state, the capture time, and the X-ray dose are also updated in the attribute information table concerning the marks that is shown in FIG. 16.

In this state, in a case in which the capture states of all of the marks that are registered in the attribute information table shown in FIG. 16 are not in the mode of "captured" when the system finish button 1504 is operated by the user, the system control section 110 displays a notification to draw user's attention to the fact that a portion which has not been treated exists. In an example shown in FIG. 21, the system control section 110 displays not-yet-captured information 2101 as a text in the region of the (not-yet-selected) mark 1503 that corresponds to a portion which has not been treated, thereby providing a notification that a (not-yet-selected) mark corresponding to a portion which has not been treated exists to the user. The system control section 110 that performs the above-mentioned notification process is configured as a notification section. Note that, in the second embodiment, the display form for notifying the user that a portion which has not been treated exists is not limited to that shown in FIG. 21. In order to notify the user that a portion which has not been treated exists, for example, the color of a mark corresponding to the portion that has not been treated may be changed, or the mark may be displayed so as to blink.

In the X-ray image capturing device 100 according to the second embodiment, in addition to the configuration in the first embodiment, the display form of a mark in the GUI 190 can be changed in accordance with the capture state of the mark.

With the above-described configuration, a state of capturing an image, which is used for treatment, of a portion to be treated, which is a portion to be subjected to surgery, i.e., whether or not an image of the portion has been captured (whether or not the portion has been treated), can be checked simply using the display form of a mark.

Furthermore, in case in which a mark that has not been selected exists among the plurality of marks that are displayed in the GUI 190 when image capturing using the capturing unit 152 finishes, the fact that a mark which has not been selected exists is notified. Accordingly, the mark that has not been selected can be prevented from being missed.

The steps shown in FIGS. 2 and 14 illustrating the methods for driving the X-ray image capturing devices (the radiographic image capturing devices) according to the above-described embodiments can be realized, for example, by executing a program that is stored in a random-access memory (RAM) or a read-only memory (ROM) with a central processing unit (CPU) of a computer. The program and a computer-readable storage medium on which the program is recorded may each be provided in another embodiment of the present invention.

More specifically, the program is recorded on a storage medium such as a compact disk read-only memory (CD-ROM), or is provided to the computer via various types of transmission media. As the storage medium on which the program is recorded, a flexible disk, a hard disk, a magnetic tape, a magneto-optical disk, a non-volatile memory card, or the like can be used instead of a CD-ROM. As the various types of transmission media for the program, communication media in a system of a computer network, which includes a local area network (LAN), a wide area network (WAN) such as the Internet, a radio communication network, and so forth, for supplying the program by transmitting program information as a carrier wave can be used. Moreover, as the communication media in this case, wire links such as optical fibers or wireless links may be used.

Furthermore, the present invention is not limited to an embodiment in which functions of the X-ray image capturing device (the radiographic image capturing device) according to any one of the above-described embodiments are realized by executing the supplied program with the computer. Also when the functions of the X-ray image capturing device (the radiographic image capturing device) according to any one of the above-described embodiments are realized by the program in collaboration with an operating system (OS) that operates in the computer, other application software, or the like, the program may be provided in another embodiment of the present invention. Additionally, also when the functions of the X-ray image capturing device (the radiographic image capturing device) according to any one of the above-described embodiments are realized by performing all of or some of processes of the supplied program with a functionally expanded board or functionally expanded unit of the computer, the program may be provided in another embodiment of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-158457, filed Jun. 17, 2008, which is hereby incorporated by reference herein in its entirety.

The invention claimed is:

1. A radiographic image capturing device comprising:
a radiation generating unit configured to emit radiation;
a capturing unit configured to capture a radiographic image of an object based on radiation that is emitted from the radiation generating unit and that penetrates through the object;
a support unit configured to support the radiation generating unit and the capturing unit;
a radiation range limiting unit that is provided between the radiation generating unit and the object, and that is configured to limit a radiation range of the radiation which is emitted from the radiation generating unit onto the object;
a display unit configured to display the radiographic image;
a mark display control unit configured to perform control of displaying a selected mark selected from among a plurality of marks on the radiographic image displayed on the display unit; and
a position control unit to control a position of the support unit in accordance with a position of the selected mark so that the capturing unit captures a radiographic image of a portion of the object that corresponds to the selected mark,
wherein the radiation range limiting unit limits the radiation range of the radiation in accordance with a shape and a size of the selected mark.

2. The radiographic image capturing device according to claim 1, further comprising:
a radiation-range control unit configured to control the radiation range limiting unit,
wherein the position control unit controls the position of the support unit in accordance with a position of the selected mark, and the radiation-range control unit controls the radiation range limiting unit to limit the radiation range in accordance with the size of the selected mark, thereby performing control of capturing the radiographic image of the portion of the object corresponding to the selected mark.

3. The radiographic image capturing device according to claim 2, further comprising a storage unit configured to store an attribute information table in which, for each of the plurality of marks that is displayed by the mark display control unit, attribute information concerning the selected mark is specified, the attribute information concerning the selected mark including information concerning the shape of the selected mark,
wherein the mark display control unit displays the selected mark in accordance with the shape that is specified in the attribute information table, and the radiation-range limiting unit controls the radiation range limiting unit in accordance with the shape that is specified in the attribute information table.

4. The radiographic image capturing device according to claim 3, wherein, in addition to the information concerning the shape of the selected mark, information concerning a position of the selected mark and information concerning a size of the selected mark are specified in the attribute information table, and the mark display control unit displays the selected mark in accordance with the shape, the position, and the size that are specified in the attribute information table.

5. The radiographic image capturing device according to claim 1, further comprising an image processing unit configured to perform image processing on the radiographic image of the object,
wherein the mark display control unit displays the selected mark on a predetermined portion of the radiographic image of the object in accordance with a result of image processing that is performed by the image processing unit.

6. The radiographic image capturing device according to claim 5, wherein, based on a position and a size of the predetermined portion of the radiographic image of the object that is used when the selected mark is displayed, the mark display control unit determines a position of a center and a size of a potential portion of the object which is to be treated.

7. The radiographic image capturing device according to claim 1, further comprising an input unit configured to be used to provide an input,
wherein the mark display control unit determines, in accordance with a position that is provided through an instruction using the input unit, a position and a size of a predetermined portion of the radiographic image of the object where the selected mark is to be displayed.

8. The radiographic image capturing device according to claim 7, wherein, based on the position and the size of the predetermined portion of the radiographic image of the object that is used when the selected mark is displayed, the mark display control unit determines a shape of a potential portion of the object which is to be treated.

9. The radiographic image capturing device according to claim 7, wherein the mark display control unit determines, in accordance with the shape of the selected mark that is provided through an instruction using the input unit, a shape that is used when the selected mark is displayed.

10. The radiographic image capturing device according to claim 1, wherein the mark display control unit changes a display form of the selected mark in accordance with a capture state of the capturing unit.

11. The radiographic image capturing device according to claim 10, wherein the mark display control unit displays the plurality of marks on a plurality of predetermined portions of the radiographic image of the object, and
wherein, when one mark is selected as the selected mark from among the plurality of marks, the capturing unit captures a radiographic image of a portion of the object that corresponds to one of the plurality of predetermined portions, the selected mark being displayed on the one of the plurality of predetermined portions.

12. The radiographic image capturing device according to claim 11, wherein the mark display control unit changes a display form of the one mark when the one mark is selected.

13. The radiographic image capturing device according to claim 11, further comprising a notification unit configured to provide, in a case in which a mark that has not been selected exists among the plurality of marks when image capturing that is performed using the capturing unit finishes, a notification that a mark which has not been selected exists.

14. The radiographic image capturing device according to claim 11, further comprising an information display control unit configured to control the display unit to display, when image capturing is performed at the selected mark, information concerning a capture time taken to perform the image capturing and information concerning a dose of radiation that is emitted in the image capturing.

15. The radiographic image capturing device according to claim 14, further comprising a storage unit configured to store an attribute information table in which, for each mark that is displayed by the mark display control unit, attribute information concerning the selected mark is specified, the attribute information concerning the selected mark including the information concerning the capture time, the information concerning the dose of radiation, and a final radiographic image in the radiographic image, and a superimposing unit configured to superimpose, when image capturing is performed by the capturing unit at the selected mark, a final radiographic image on a predetermined portion of the radiographic image on which the selected mark is displayed, the final radiographic image being captured at the selected mark.

16. A method for driving a radiographic image capturing device to capture a radiographic image, the method comprising:

irradiating an object with radiation emitted from a radiation generating unit;

a capturing step of capturing a radiographic image of the object with a capturing unit based on the radiation emitted from the radiation generating unit and that penetrates through the object;

a radiation range limiting step of limiting a radiation range of the radiation which is emitted from the radiation generating unit onto the object, by using a radiation range limiting unit that is provided between the radiation generating unit and the object;

a display step of displaying the radiographic image on a display unit;

a mark display control step of performing control of displaying a selected mark selected from among a plurality of marks on the radiographic image displayed on the display unit; and a position control step of controlling a position of a support unit in accordance with a position of the selected mark so that the capturing unit captures a radiographic image of a portion of the object that corresponds to the selected mark, wherein in the radiation range limiting step, the radiation range limiting unit limits the radiation range of the radiation in accordance with a shape and a size of the selected mark.

17. A radiographic image capturing device comprising:

a radiation generating unit configured to emit radiation;

a capturing unit configured to capture a radiographic image of an object based on radiation that is emitted from the radiation generating unit and that penetrates through the object;

a radiation range limiting unit that is provided between the radiation generating unit and the object, and that is configured to limit a radiation range of the radiation which is emitted from the radiation generating unit onto the object;

a display unit configured to display the radiographic image;

a mark display control unit configured to perform control of displaying a selected mark selected from among a plurality of marks on the radiographic image displayed on the display unit;

wherein the radiation range limiting unit limits the radiation range of the radiation in accordance with a shape and a size of the selected mark so that the capturing unit captures a radiographic image of a portion of the object that corresponds to the selected mark;

a storage unit configured to store an attribute information table in which, for each of the plurality of marks that is displayed by the mark display control unit, attribute information concerning the selected mark is specified, and a superimposing unit configured to superimpose, when image capturing is performed by the capturing unit at a position of the selected mark, the radiographic image on the selected mark.

* * * * *